United States Patent
Katori et al.

(10) Patent No.: US 11,413,227 B2
(45) Date of Patent: Aug. 16, 2022

(54) DURABLE SUNSCREEN COSMETIC

(71) Applicant: SHISEIDO COMPANY, LTD., Tokyo (JP)

(72) Inventors: Takahiro Katori, Yokohama (JP); Satoshi Yamaki, Yokohama (JP); Kouichi Nagai, Yokohama (JP); Yurika Watanabe, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 84 days.

(21) Appl. No.: 16/641,937

(22) PCT Filed: Aug. 23, 2018

(86) PCT No.: PCT/JP2018/031168
§ 371 (c)(1),
(2) Date: Feb. 25, 2020

(87) PCT Pub. No.: WO2019/039548
PCT Pub. Date: Feb. 28, 2019

(65) Prior Publication Data
US 2020/0246234 A1 Aug. 6, 2020

(30) Foreign Application Priority Data
Aug. 25, 2017 (JP) .............................. JP2017-162724

(51) Int. Cl.
A61K 8/27 (2006.01)
A61K 8/02 (2006.01)
A61K 8/25 (2006.01)
A61K 8/28 (2006.01)
A61K 8/96 (2006.01)

(52) U.S. Cl.
CPC ............... *A61K 8/27* (2013.01); *A61K 8/022* (2013.01); *A61K 8/25* (2013.01); *A61K 8/28* (2013.01); *A61K 8/965* (2013.01)

(58) Field of Classification Search
CPC .............................. A61K 8/022; A61K 8/0254
See application file for complete search history.

(56) References Cited

U.S. PATENT DOCUMENTS

| 8,673,329 | B2 | 3/2014 | Yamada et al. | |
| 2010/0233103 | A1* | 9/2010 | Shirao | A61Q 17/04 424/59 |
| 2011/0274632 | A1* | 11/2011 | Ishitobi | A61K 8/89 424/60 |
| 2013/0344013 | A1 | 12/2013 | Ikebe et al. | |
| 2014/0030298 | A1 | 1/2014 | Harada et al. | |
| 2015/0030768 | A1* | 1/2015 | Ono | A61K 8/23 427/220 |

FOREIGN PATENT DOCUMENTS

| JP | H 8-188723 | 7/1996 |
| JP | H 8-217619 | 8/1996 |
| JP | 2002-020217 | 1/2002 |
| JP | 2004-002274 | 1/2004 |
| JP | 2005-015437 | 1/2005 |
| JP | 2005-298475 | 10/2005 |
| JP | 2005-350367 | 12/2005 |
| JP | 2008-508323 | 3/2008 |
| JP | 2010-059076 | 3/2010 |
| JP | 2010-168302 | 8/2010 |
| JP | 2011-236201 | 11/2011 |
| JP | 2012-001440 | 1/2012 |
| JP | 2013-151436 | 8/2013 |
| WO | WO 2016/068298 | 5/2016 |

OTHER PUBLICATIONS

European Patent Appln. Serial No. EP 18847319.3, Extended European Search Report dated Apr. 23, 2021, 6 pages—English.
PCT/JP2018/031168 International Search Report (ISR) and Written Opinion (WO), dated Nov. 27, 2018, 3 pages—English, 5 pages—Japanese.

* cited by examiner

*Primary Examiner* — Michael B. Pallay
(74) *Attorney, Agent, or Firm* — Andrew F. Young; Nolte Lackenbach Siegel

(57) ABSTRACT

The invention provides a cosmetic having strong resistance to contact with water, clothing, fingers, and abrasion with little decline (post-contact) in the cosmetic effects such as UV blocking protection as well as excellent feel on use. The cosmetic contains: (A) plate-shaped powder, (B) 6-40% by mass UV absorber, and (C) cationic surfactant.

2 Claims, No Drawings

DURABLE SUNSCREEN COSMETIC

CROSS REFERENCE TO RELATED APPLICATIONS

This application relates to and claims priority as a § 371 national phase, from PCT/JP2018/031168 filed Aug. 23, 2018, the entire contents of which are incorporated herein by reference, which in turn claims priority from JP Ser. No.: 2017-162724 filed Aug. 25, 2017.

FIGURE SELECTED FOR PUBLICATION

None

TECHNICAL FIELD

The present invention relates to a cosmetic that does not tend to come off even when coming into contact with water, clothes, fingers or the like, that suppresses decreases in makeup effects such as ultraviolet blocking functions, and that also has an excellent feeling in use.

BACKGROUND ART

A cosmetic that is applied to skin may run off due to perspiration secreted from the skin or moisture from the external environment, or may come off due to contact with clothes or fingers, thereby decreasing the makeup effects. Thus, there have been various attempts to make the makeup effects of applied cosmetics last for a long time.

Recently, sunscreen cosmetics having the unique effects in which, even when coming into contact with perspiration or moisture, the ultraviolet blocking function does not deteriorate and rather conversely increase (hereinafter sometimes referred to as "ultraviolet blocking performance improvement effects") have been developed (Patent Document 1).

However, even with oil-based or water-in-oil emulsion cosmetics that are generally considered to have excellent water resistance, the makeup may come off by coming into contact with clothes and fingers. Therefore, there has been a proposal to enhance the resistance to rubbing (friction) by strengthening the cosmetic coating film by blending a film-forming agent into the cosmetic (Patent Document 2).

However, when a silicone resin, a film-forming agent or the like, is added in a high-concentration, there are problems such as the filminess of the applied cosmetic becoming strong in some cases, the texture becoming worse, and furthermore, the cosmetic not being easily removable with a normal cleanser or soap, thus requiring a special cleansing agent or the like to be used.

RELATED ART

Patent Documents

Patent Document 1: WO 2016/068298
Patent Document 2: JP H8-217619 A

SUMMARY OF THE INVENTION

Problem to be Solved by the Invention

An objective of the present invention is to provide a cosmetic that exhibits strong resistance to contact with water, clothes, fingers and the like, that is not susceptible to decreases in makeup effects such as the ultraviolet blocking function even after contacted, and that has an excellent feeling in use.

Means for Solving the Problem

As a result of carrying out diligent investigations towards solving the aforementioned problem, the present inventors discovered that, by blending a flaky powder and a specific cationic surfactant into a cosmetic, the resistance of the coating layer to rubbing is made stronger and the cosmetic coating film does not tend to come off, so that the makeup effects such as the ultraviolet blocking function and the like do not decrease even after being rubbed. Thus, the present invention was completed.

In other words, the present invention provides a cosmetic comprising:
(A) a flaky powder;
(B) 6% to 40% by mass of an ultraviolet absorbing agent; and
(C) a cationic surfactant.

Effects of the Invention

Due to the above-mentioned features, the present invention exhibits strong resistance to contact (friction) with water, clothes, fingers or the like, and can suppress decreases in makeup effects such as ultraviolet blocking functions after contact. Furthermore, the blended amount of the film-forming agent can be reduced in comparison to conventional rubbing resistant cosmetics, so that the present invention has little shininess or stickiness after coating, and has an excellent feeling in use.

MODES FOR CARRYING OUT THE INVENTION

As mentioned above, the cosmetic of the present invention is characterized by comprising (A) a flaky powder, (B) an ultraviolet absorbing agent, and (C) a cationic surfactant. Hereinafter, the respective components constituting the cosmetic of the present invention will be explained in detail.

<(A) Flaky Powder>

As the (A) flaky powder (hereinafter sometimes referred to simply as "component (A)") blended into the cosmetic according to the present invention, it is possible to use any powder that is normally blended into cosmetics, as along as it is in flaky form, and examples thereof include inorganic powders and organic powders.

As inorganic powders, it is possible to use, in a discretionary manner, either natural or synthetic powders. Examples include, but are not limited to, silicic acid, silicic anhydride (silica gel), magnesium silicate, talc, kaolin, mica, bentonite, titanium-coated mica, bismuth oxychloride, zirconium oxide, magnesium oxide, zinc oxide, titanium dioxide, aluminum oxide, calcium sulfate, barium sulfate, magnesium sulfate, calcium carbonate, magnesium carbonate, iron oxide, ultramarine blue, Prussian blue, chromium oxide, chromium hydroxide, carbon black, complexes of the above and the like. These powders may have an ultraviolet scattering effect.

Examples of organic powders include, but are not limited to, polyamides, polyesters, polyethylenes, polypropylenes, polystyrenes, polyurethanes, vinyl resins, epoxy resins, polycarbonate resins, divinylbenzene/styrene copolymers, copolymers comprising two or more types of monomers among the above-mentioned compounds, celluloids, acetylcellulose, cellulose, polysaccharides and the like.

The flaky powder in the present invention has an average particle size of 1 to 100 μm, measured by laser diffraction, and a ratio of 2 to 200 between the long-side length (a) and the thickness (b) (i.e., aspect ratio a/b).

The flaky powder used in the present invention may be hydrophobically surface-treated. There is no particular restriction on the hydrophobic surface treatment, but examples include silicone treatments (treatments with silicone oils such as methyl hydrogen polysiloxane, dimethyl polysiloxane and methylphenyl polysiloxane; alkyl silanes such as methyl trimethoxysilane, ethyl trimethoxysilane, hexyl trimethoxysilane and octyl trimethoxysilane; and fluoroalkyl silanes such as trifluoromethylethyl trimethoxysilane and heptadecafluorodecyl trimethoxysilane), fatty acid treatments (treatments with palmitic acid, isostearic acid, stearic acid, lauric acid, myristic acid, behenic acid, oleic acid, rosin acid, 12-hydroxystearic acid and the like), fatty acid soap treatments (treatments with aluminum stearate, calcium stearate, 12-hydroxystearic acid and the like), fatty acid ester treatments (treatments with dextrin fatty acid esters, cholesterol fatty acid esters, sucrose fatty acid esters, starch fatty acid esters and the like) and the like. Among the above, treatments with dimethyl polysiloxane or calcium stearate are particularly preferred. These hydrophobic treatments may be performed by means of conventional methods.

The flaky powder used in the present invention may be produced from a raw material mineral by means of a normal method, preferably wet-grinding, or a commercially available product may be used as is.

The flaky powder used in the present invention is preferably talc or mica in view of the resistance to rubbing (friction resistance) and emulsion stability. By including these powders, it is possible to raise the resistance to rubbing.

Examples of preferred commercially available products include the Talclear LH series (manufactured by Nippon Talc), the Silky Talc series (manufactured by Yamaguchi Mica), the Fit Powder series (manufactured by Yamaguchi Mica), the Talc JET for Cosmetics series (manufactured by Asada Seifun) and the like.

The blended amount of component (A) should be 1% to 30% by mass relative to the total amount of the cosmetic, preferably 2% to 20% by mass, more preferably 3% to 15% by mass and even more preferably 4% to 10% by mass. If the blended amount of component (A) is less than 1% by mass, then sufficient resistance to rubbing (friction) cannot be obtained, and if more than 30% by mass is blended, then the stability becomes poor, so it is not favorable for the blended amount to be in these ranges.

<(B) Ultraviolet Absorbing Agent>

As the (B) ultraviolet absorbing agent (hereinafter sometimes referred to simply as "component (B)") blended into the cosmetic according to the present invention, it is possible to use any type that is normally blended into sunscreen cosmetics.

The ultraviolet absorbing agent is not particularly limited, but a broad range of ultraviolet absorbing agents that are generally used in cosmetics may be mentioned as examples. Specific examples include benzoic acid derivatives, salicylic acid derivatives, cinnamic acid derivatives, dibenzoylmethane derivatives, β,β-diphenyl acrylate derivatives, benzophenone derivatives, benzylidene camphor derivatives, phenylbenzimidazole derivatives, triazine derivatives, phenylbenzotriazole derivatives, anthranil derivatives, imidazoline derivatives, benzalmalonate derivatives, 4,4-diarylbutadiene derivatives and the like.

Examples of benzoic acid derivatives include ethyl para-aminobenzoate (PABA), ethyl-dihydroxypropyl PABA, ethylhexyl-dimethyl PABA, glyceryl PABA, PEG-25-PABA, diethylamino hydroxybenzoyl hexyl benzoate and the like.

Examples of salicylic acid derivatives include homosalate, ethylhexyl salicylate, dipropylene glycol salicylate, TEA salicylate and the like.

Examples of cinnamic acid derivatives include octyl methoxycinnamate or ethylhexyl methoxycinnamate, isopropyl methoxycinnamate, isoamyl methoxycinnamate, cinoxate, DEA methoxycinnamate, diisopropyl methylcinnamate, glyceryl ethylhexanoate dimethoxycinnamate, di-(2-ethylhexyl)-4'-methoxybenzalmalonate and the like.

Examples of dibenzoyl methane derivatives include 4-tert-butyl-4'-methoxy dibenzoyl methane and the like.

Examples of β,β-diphenyl acrylate derivatives include octocrylene and the like.

Examples of benzophenone derivatives include benzophenone-1, benzophenone-2, benzophenone-3 or oxybenzone, benzophenone-4, benzophenone-5, benzophenone-6, benzophenone-8, benzophenone-9, benzophenone-12 and the like.

Examples of benzylidene camphor derivatives include 3-benzylidene camphor, 4-methylbenzylidene camphor, benzylidene camphor sulfonic acid, camphor benzalkonium methosulfate, terephthalylidene dicamphor sulfonic acid, polyacrylamide methylbenzylidene camphor and the like.

Examples of phenylbenzimidazole derivatives include phenylbenzimidazole sulfonic acid, disodium phenyldibenzimidazole tetrasulfonate and the like.

Examples of triazine derivatives include bis-ethylhexyloxyphenol methoxyphenyl triazine, ethylhexyl triazone, diethylhexyl butamido triazone, 2,4,6-tris(diisobutyl-4'-aminobenzalmalonate)-s-triazine, 2,4,6-tris[4-(2-ethylhexyloxycarbonyl)anilino]-1,3,5-triazine and the like.

Examples of phenylbenzotriazole derivatives include drometrizole trisiloxane, methylene bis(benzotriazolyl tetramethylbutyl phenol) and the like.

Examples of anthranil derivatives include menthyl anthranilate and the like.

Examples of imidazoline derivatives include ethylhexyl dimethoxybenzylidene dioxoimidazoline propionate and the like.

Examples of benzalmalonate derivatives include polyorganosiloxanes having benzalmalonate functional groups and the like.

Examples of 4,4-diarylbutadiene derivatives include 1,1-dicarboxy (2,2'-dimethylpropyl)-4,4-diphenylbutadiene and the like.

The blended amount of component (B) should be 6% to 40% by mass relative to the total amount of the cosmetic, more preferably 7% to 35% by mass and even more preferably 8% to 30% by mass. If the blended amount of component (B) is less than 6% by mass, then sufficient ultraviolet blocking effects cannot be obtained, and if more than 40% by mass is blended, then an increase in the ultraviolet blocking effects that is commensurate with the blended amount cannot be expected and the stability becomes poor, so it is not favorable for the blended amount to be in these ranges. As component (B), it is possible to use one type alone, or to use a combination of two or more types.

<(C) Cationic Surfactant>

The (C) cationic surfactant (hereinafter sometimes referred to simply as "component (C)") blending into the cosmetic according to the present invention is preferably a surfactant that is an organic amine or a salt thereof, a surfactant that is a quaternary ammonium or a salt thereof, or the like. As specific examples, it is preferably to use one or more types selected from among lauryl trimethyl ammonium chloride, cetyl trimethyl ammonium chloride (cetrimonium chloride), stearyl trimethyl ammonium chloride (steartrimonium chloride), alkyl trimethyl ammonium chloride, behenyl trimethyl ammonium chloride (behentrimonium chloride), distearyl dimonium chloride (distearyl dimethyl ammonium chloride), dicocoyl dimethyl ammonium chloride, cetyl trimethyl ammonium bromide, stearyl trimethyl ammonium bromide, lanolin fatty acid aminopropylethyldimethyl ammonium ethyl sulfate, stearyl trimethyl ammonium saccharin, cetyl trimethyl ammonium saccharin, behenyl trimethyl ammonium methyl sulfate, quaternium-91 and the like. Among these cationic surfactants, quaternary ammonium salt-type cationic surfactants are preferred, and distearyl dimonium chloride is particularly preferred.

The blended amount of component (C) should be 0.1% to 3% by mass relative to the total amount of the cosmetic, preferably 0.15% to 2% by mass and more preferably 0.2% to 1% by mass. If the blended amount of component (C) is less than 0.1% by mass, then enough resistance against bathing and rubbing cannot be obtained, and if more than 3% by mass is blended, then the texture is poor, due to, such as an occurrence of stickiness, so it is not favorable for the blended amount to be in these ranges.

It is preferable to further blend a (D) ultraviolet scattering agent (hereinafter sometimes referred to simply as "component (D)") into the cosmetic according to the present invention for the purposes of further improving the ultraviolet blocking effect and the resistance to rubbing. The ultraviolet scattering agent used in the present invention is not particularly limited, and specific examples include zinc oxide, titanium oxide, iron oxide, cerium oxide, tungsten oxide and the like. For having both ultraviolet blocking power and transparency, titanium oxide and zinc oxide are preferred. Furthermore, zinc oxide is most preferred for purposes of resistance to rubbing. Additionally, an ultraviolet scattering agent having any shape, such as lump-shape, scale-shape, spherical shape, porous spherical or petal-shape, may be used. However, those that are flaky are not included in component (D). Additionally, the particle size is also not particularly restricted.

The ultraviolet scattering agent may be non-surface-treated, or may be hydrophobically surface-treated by various methods, but those that are hydrophobically surface-treated are preferred, and the hydrophobic surface treating agent may be of any type that is generally used in the cosmetic field. For example, it is possible to use a silicone such as dimethicone or alkyl-modified silicone, an alkoxysilane such as octyl triethoxysilane, a dextrin fatty acid ester such as dextrin palmitate, or a fatty acid such as stearic acid.

The blended amount of component (D) should be 1% to 30% by mass relative to the total amount of the cosmetic, preferably 3% to 20% by mass and more preferably 5% to 15% by mass. If the blended amount of component (D) is less than 1% by mass, then further improvement in ultraviolet blocking effects and resistance effects against rubbing cannot be obtained, and if more than 30% by mass is blended, then the stability becomes poor, so it is not favorable for the blended amount to be in these ranges.

In the cosmetic according to the present invention, it is preferable to blend, in addition to the above-mentioned components (A), (B) and (C), for the purposes of obtaining an ultraviolet blocking performance improvement effect, (E) an organically modified clay mineral, (F) a surfactant other than the above-mentioned component (C), and (G) an oil phase thickener.

As the (E) organically modified clay mineral (hereinafter sometimes referred to simply as "component (E)") blended into the cosmetic according to the present invention, it is possible to use a clay mineral modified by a quaternary ammonium salt type cationic surfactant, represented by the following general formula (1), which is a type of colloidal hydrated ammonium silicate having a three-layered structure.

$$(X,Y)_{2-3}(Si,Al)_4O_{10}(OH)_2Z_{1/3} \cdot nH_2O \tag{1}$$

where X=Al, Fe(III), Mn(III) or Cr(III); Y=Mg, Fe(II), Ni, Zn or Li; and Z=K, Na or Ca.

Specifically, the organically modified clay mineral can be obtained by treating, with a quaternary ammonium salt type cationic surfactant, a clay mineral which may be a natural or synthetic (in this case, an (OH) group in the formula is substituted with a fluorine) clay mineral in the montmorillonite group, such as montmorillonite, saponite or hectorite (commercial products include Veegum®, Kunipia, Laponite®, etc.), or a synthetic mica known under the name of sodium silicic mica or sodium or lithium taeniolite (commercial products include Dimonite, manufactured by Topy Industries, Ltd. etc.).

The quaternary ammonium salt type cationic surfactant used in this case is represented by the following general chemical formula (2):

[Chemical Formula 2]

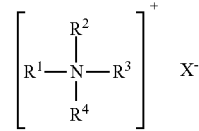

$$\left[ R^1 - \underset{\underset{R^4}{|}}{\overset{\overset{R^2}{|}}{N}} - R^3 \right]^+ X^- \tag{2}$$

where $R^1$ represents a benzyl group or an alkyl group having 10 to 22 carbon atoms, $R^2$ represents an alkyl group having 10 to 22 carbon atoms or a methyl group, $R^3$ and $R^4$ represent hydroxyalkyl groups or alkyl groups having 1 to 3 carbon atoms, and X represents a halogen atom or a methylsulfate residue.

Examples of the quaternary ammonium salt type cationic surfactant include dodecyl trimethyl ammonium chloride, myristyl trimethyl ammonium chloride, cetyl trimethyl ammonium chloride, stearyl trimethyl ammonium chloride, arachyl trimethyl ammonium chloride, behenyl trimethyl ammonium chloride, myristyl dimethyl ethyl ammonium chloride, cetyl dimethyl ethyl ammonium chloride, stearyl dimethyl ethyl ammonium chloride, arachyl dimethyl ethyl ammonium chloride, behenyl dimethyl ethylammonium chloride, myristyl diethyl methyl ammonium chloride, cetyl diethyl methyl ammonium chloride, stearyl diethyl methyl ammonium chloride, arachyl diethyl methyl ammonium chloride, behenyl diethyl methyl ammonium chloride, benzyl dimethyl myristyl ammonium chloride, benzyl dimethyl cetyl ammonium chloride, benzyl dimethyl stearyl ammonium chloride, benzyl dimethyl behenyl ammonium chloride, benzyl methyl ethyl cetyl ammonium chloride, benzyl methyl ethyl stearyl ammonium chloride, dibehenyl dihydroxyethyl ammonium chloride, and corresponding bromides and the like, and further thereto, dipalmityl propyl ethyl ammonium methyl sulfate and the like. When carrying out the present invention, one or more of these compounds may be arbitrarily selected.

Representative examples of component (E) include dimethyl distearyl ammonium hectorite (distearyl dimonium hectorite), dimethyl alkyl ammonium hectorite, benzyl dimethyl stearyl ammonium hectorite, distearyl dimethyl ammonium chloride-treated aluminum-magnesium silicate and the like. Of these, dimethyl distearyl ammonium hectorite is particularly preferred. As commercial products, Bentone 27 (benzyl dimethyl stearyl ammonium chloride-treated hectorite, manufactured by Elementis Japan KK) and Bentone 38 (distearyl dimethyl ammonium chloride-treated hectorite, manufactured by Elementis Japan KK) are preferred.

The blended amount of component (E) should be 0.1% to 3% by mass relative to the total amount of the cosmetic, preferably 0.2% to 2.5% by mass. If the blended amount of component (E) is less than 0.1% by mass, then ultraviolet blocking performance improvement effects cannot be obtained, and if more than 3% by mass is blended, then the viscosity becomes high and the texture is affected, such as the cosmetic becoming difficult to spread on the skin, so it is not favorable for the blended amount to be in these ranges.

The (F) surfactant (hereinafter sometimes referred to simply as "component (F)") that is further blended in the cosmetic of the present invention refers to a surfactant other than a cationic surfactant, and is preferably a surfactant, particularly a silicone-based surfactant, having an HLB lower than 8, in order to realize an emulsion form.

Examples of silicone-based surfactants having an HLB lower than 8 include polyoxyalkylene-modified silicones, polyoxyalkylene/alkyl co-modified silicones, polyglycerin-modified silicones and/or polyglycerin/alkyl co-modified silicones. Specific examples include KF-6017 (PEG-10 dimethicone, manufactured by Shin-etsu Chemical Co., Ltd.), KF-6028 (PEG-9 polydimethylsiloxyethyl dimethicone, manufactured by Shin-etsu Chemical Co., Ltd.), ABIL EM 90 (cetyl PEG/PPG-10/1 dimethicone, manufactured by Evonik Goldschmidt Corp.) and KF-6038 (lauryl PEG-9 polydimethylsiloxyethyl dimethicone, manufactured by Shin-etsu Chemical Co., Ltd.), bis-butyl dimethicone polyglyceryl-3 and the like.

The blended amount of component (F) should be 0.1% to 8% by mass relative to the total amount of the cosmetic, preferably 0.2% to 7% by mass, more preferably 0.4% to 5% by mass, and even more preferably 0.6% to 3% by mass.

The (G) oil phase thickener (hereinafter sometimes referred to simply as "component (G)") blended in the cosmetic of the present invention is a substance, other than component (E) of the present invention, that is able to adjust the viscosity of the oil phase. Examples include dextrin fatty acid esters, sucrose fatty acid esters, fatty acids or salts thereof, hardened vegetable oils, solid or semi-solid vegetable oils and the like.

Dextrin fatty acid esters are esters of dextrin or reduced dextrin with a higher fatty acid, which may be used without any particular restrictions as long as they are generally used in cosmetics. As the dextrin or reduced dextrin, one in which the average degree of sugar polymerization is 3 to 100 is preferably used. Additionally, as the constituent fatty acids in the dextrin fatty acid ester, a saturated fatty acid having 8 to 22 carbon atoms is preferably used. Specific examples include dextrin palmitate, dextrin oleate, dextrin stearate, dextrin myristate, dextrin (palmitate/2-ethylhexanoate) and the like.

As the sucrose fatty acid esters, those in which the fatty acid is linear or branched, saturated or unsaturated, and having 12 to 22 carbon atoms are preferably used. Specific examples include sucrose caprylic acid esters, sucrose capric acid esters, sucrose lauric acid esters, sucrose myristic acid esters, sucrose palmitic acid esters, sucrose stearic acid esters, sucrose oleic acid esters, sucrose erucic acid esters, sucrose acetate/stearate and the like.

The fatty acids that is solid at ambient temperature can be used, and examples thereof include myristic acid, palmitic acid, stearic acid, behenic acid and the like. Additionally, the fatty acid salts may be calcium salts, magnesium salts, aluminum salts or the like of the above.

Examples of the hardened vegetable oil include hardened palm kernel oil, hardened castor oil, hydrogenated peanut oil, hydrogenated rapeseed oil, hydrogenated palm oil, hydrogenated camellia oil, hydrogenated soybean oil, hydrogenated olive oil, hydrogenated macadamia nut oil, hydrogenated sunflower oil, hydrogenated wheat germ oil, hydrogenated rice germ oil, hydrogenated rice bran oil, hydrogenated cottonseed oil, hydrogenated avocado oil and the like.

Additionally, like the hardened vegetable oils, it is also possible to use a vegetable oil that is solid or semi-solid at room temperature. In this case, a solid oil refers to an oil that is solid at 25° C., and a semi-solid oil refers to an oil in which half the amount thereof is solid at 25° C. More specifically, one in which the melting point is in the range from 44° C. to 90° C., the viscosity measured with a B-type viscometer at 25° C. is 5000 mPa·s or higher, or furthermore, 10,000 mPa·s or higher, is preferred. Examples of vegetable oils that are solid or semi-solid at room temperature include cacao butter, coconut oil, palm oil, palm kernel oil, Japan tallow, shea butter and the like.

The blended amount of component (G) should be 0.1% to 15% by mass relative to the total amount of the cosmetic, preferably 0.2% to 10% by mass, more preferably 0.4% to 8% by mass, and even more preferably 0.5% to 4% by mass. As component (G) used in the cosmetic of the present invention, it is preferable to use a dextrin fatty acid ester.

Aside from the above-mentioned essential components, the cosmetic of the present invention may arbitrarily comprise, as needed, components that are normally used in cosmetics such as, for example, oils, water, alcohols, oil-based active agents, water-based active agents, thickeners, humectants, whiteners, antioxidants and the like, within a range not interfering with the effects of the present invention.

In the cosmetic of the present invention, the blended amount of the film-forming agent is preferably 3% by mass or less, and more preferably 1% by mass or less for the purposes of the texture.

The cosmetic of the present invention can be produced by a conventional method in a form such as a water-in-oil emulsion cosmetic, an oil-based cosmetic, an oil-in-water emulsion cosmetic, an oil-in-water emulsion cosmetic in which, for example, a powder component is blended into the oil component, or the like. Among these, a water-in-oil emulsion cosmetic is preferred.

The cosmetic of the present invention may be provided not only, for example, as a sunscreen cream, a sunscreen milky lotion or a sunscreen lotion, but may also be used as a foundation, a makeup base, a makeup cosmetic, a hair cosmetic or the like imparted with sunscreen effects, and may be produced by a conventional method.

EXAMPLES

The present invention will be explained in further detail by referring to specific examples below, but the present invention is not limited to the examples indicated below. Additionally, the blended amounts in the following examples and the like are in percentage by mass unless specially indicated otherwise.

Examples 1, 2, 5 and 6, and Comparative Examples 1 to 3

The cosmetics having the compositions indicated in Table 1 below were prepared by heating and dissolving the oil-based components, dispersing the powders therein, adding the separately dissolved water phase, and emulsifying in a stirring process.

Method for Measuring a Percentage of Residual Ultraviolet Blocking Effect

Each example sample was dropped to make a rate of 2 mg/cm² onto S plates (5×5 cm V-groove PMMA plates, SPFMASTER-PA01), coated using a finger in 60 seconds, and dried for 15 minutes, and then the absorbances (in the range of 400 to 280 nm) thereof were measured using the Hitachi U-3500 self-recording spectrophotometer. An uncoated plate was used as the control, and the absorbances (Abs) were computed by using the following formula.

$$Abs = -\log(T/T_0)$$

T: transmittance of the coated sample plate, To: transmittance of uncoated plate Next, the measured plates were immersed in water, the S plates were placed with the coated surfaces facing upwards, tissue paper was wrapped onto a finger, and the plates were rubbed with a constant pressures and a constant number of times. Thereafter, the absorbances of the S plates were again measured with the spectrophotometer.

Based on the respective absorbances (integral values) immediately after applying the cosmetics and after bathing and rubbing the cosmetics with tissues, the percentage of residual makeup effect after bathing and rubbing was determined using the following formula. If the percentage is less than 100%, then this indicates that the makeup effect (ultraviolet blocking performance) of the cosmetic decreases compared to that immediately after application, whereas if the percentage is more than 100%, then this indicates that the makeup effect of the cosmetic increases compared to that immediately after application.

Percentage of residual makeup effect (%)={(integral value of absorbance after rubbing with tissue)/(integral value of absorbance immediately after application)}×100

TABLE 1

|  | Ex. 1 | Ex. 2 | Ex. 5 | Ex. 6 | Comp. Ex. 1 | Comp. Ex. 2 | Comp. Ex. 3 |
| --- | --- | --- | --- | --- | --- | --- | --- |
| Hydrophobically treated talc | 7 | 7 | 4 | 10 | — | 7 | — |
| Methyl methacrylate cross-polymer | 5 | 5 | 5 | 5 | 5 | 5 | 12 |
| Hydrophobically treated zinc oxide | 10 | — | 10 | 10 | 10 | 10 | 10 |
| Hydrophobically treated titanium oxide | 2 | — | 2 | 2 | 2 | 2 | 2 |
| Octocrylene | 3 | 3 | 3 | 3 | 3 | 3 | 3 |
| Ethylhexyl methoxycinnamate | 7 | 7 | 7 | 7 | 7 | 7 | 7 |
| bis-Ethylhexyloxyphenol methoxyphenyl triazine | 1 | 1 | 1 | 1 | 1 | 1 | 1 |
| Diethylaminohydroxybenzoyl hexyl benzoate | 1 | 1 | 1 | 1 | 1 | 1 | 1 |
| Distearyl dimonium chloride | 0.5 | 0.5 | 0.5 | 0.5 | 0.5 | — | 0.5 |
| PEG-9 polydimethylsiloxyethyl dimethicone | 1.5 | 1.5 | 1.5 | 1.5 | 1.5 | 1.5 | 1.5 |
| Distearyl dimonium hectorite | 0.5 | 0.5 | 0.5 | 0.5 | 0.5 | 0.5 | 0.5 |
| Dextrin palmitate | 1 | 1 | 1 | 1 | 1 | 1 | 1 |
| PPG-17 | 1 | 1 | 1 | 1 | 1 | 1 | 1 |
| Trimethylsiloxysilicic acid | 1 | 1 | 1 | 1 | 1 | 1 | 1 |
| Isododecane | 3 | 3 | 3 | 3 | 3 | 3 | 3 |
| Dimethicone | 23 | 23 | 23 | 23 | 23 | 23 | 23 |
| Isostearic acid | 1 | 1 | 1 | 1 | 1 | 1 | 1 |
| Isopropyl myristate | 5 | 5 | 5 | 5 | 5 | 5 | 5 |
| Glycerin | 1 | 1 | 1 | 1 | 1 | 1 | 1 |
| Xylitol | 1 | 1 | 1 | 1 | 1 | 1 | 1 |
| Ethanol | 10 | 10 | 10 | 10 | 10 | 10 | 10 |
| EDTA-3Na | s.a. | s.a. | s.a. | s.a. | s.a. | s.a. | s.a. |
| Sodium chloride | s.a. | s.a. | s.a. | s.a. | s.a. | s.a. | s.a. |
| Water | bal | bal | bal | bal | bal | bal | bal |
| Percentage of residual makeup effect (%) | 105 | 101 | 103 | 105 | 92 | 96 | 97 |

As shown in Table 1, the makeup effects of a cosmetic not containing an (A) flaky powder (Comparative Example 1) and a cosmetic not containing a (C) cationic surfactant (Comparative Example 2) decreased from those immediately after application of the cosmetic due to bathing and rubbing. Additionally, even when the total amount of the powder was the same, the makeup effect of a cosmetic containing only a spherical powder (Comparative Example 3) decreased due to bathing and rubbing.

In contrast therewith, the makeup effects, represented by the ultraviolet blocking performance, of cosmetics comprising the components (A), (B) and (C) of the present invention (Examples 1 and 2) were sufficiently maintained even after bathing and rubbing, and in fact, the ultraviolet blocking effects were higher than those immediately after applying the cosmetic. Thus, it was shown that the cosmetic of the present invention has high resistance to water and rubbing (friction). Additionally, the cosmetics of Examples 1, 2, 5 and 6 had good stability and had an excellent feeling in use.

Next, the cosmetic of Example 1 was evaluated, based on the following criteria, regarding the feeling in use (stickiness) when the blended amount of the film-forming agent (trimethylsiloxysilicic acid) was increased. The results are shown in Table 2.

<Evaluation Criteria>

A: 8 or more of 10 panelists replied that there was no stickiness.

B: 4 to 7 of 10 panelists replied that there was no stickiness.

C: 0 to 3 of 10 panelists replied that there was no stickiness.

TABLE 1

| | Ex. 1 | Ex. 3 | Ex. 4 |
|---|---|---|---|
| Hydrophobically treated talc | 7 | 7 | 7 |
| Methyl methacrylate cross-polymer | 5 | 5 | 5 |
| Hydrophobically treated zinc oxide | 10 | 10 | 10 |
| Hydrophobically treated titanium oxide | 2 | 2 | 2 |
| Octocrylene | 3 | 3 | 3 |
| Ethylhexyl methoxycinnamate | 7 | 7 | 7 |
| bis-Ethylhexyloxyphenol methoxyphenyl triazine | 1 | 1 | 1 |
| Diethylaminohydroxybenzoyl hexyl benzoate | 1 | 1 | 1 |
| Distearyl dimonium chloride | 0.5 | 0.5 | 0.5 |
| PEG-9 polydimethylsiloxyethyl dimethicone | 1.5 | 1.5 | 1.5 |
| Distearyl dimonium hectorite | 0.5 | 0.5 | 0.5 |
| Dextrin palmitate | 1 | 1 | 1 |
| PPG-17 | 1 | 1 | 1 |
| Trimethylsiloxysilicic acid | 1 | 3 | 5 |
| Isododecane | 3 | 3 | 3 |
| Dimethicone | 23 | 23 | 23 |
| Isostearic acid | 1 | 1 | 1 |
| Isopropyl myristate | 5 | 5 | 5 |
| Glycerin | 1 | 1 | 1 |
| Xylitol | 1 | 1 | 1 |
| Ethanol | 10 | 10 | 10 |
| EDTA-3Na | s.a. | s.a. | s.a. |
| Sodium chloride | s.a. | s.a. | s.a. |
| Water | bal | bal | bal |
| No stickiness | A | B | C |

All cosmetics according to Examples 1, 3 and 4 exhibited a good resistance to rubbing. As shown in Table 2, when the blended amount of the film-forming agent was low (Example 1), there was little stickiness and the cosmetic having the best texture was obtained. However, as the blended amount of the film-forming agent was increased (Example 3 and Example 4), there was a tendency to feel stickiness.

FORMULATION EXAMPLES

Hereinafter, formulation examples of the cosmetic of the present invention will be described. The blended amounts are all indicated in percentage by mass relative to the total amount of the product.

Production Method

Regarding tables 3 to 8 below, the oil phase components among the components indicated in the tables were homogeneously heated and mixed to prepare an oil phase part, and the powder components were dispersed in this oil phase part to obtain a mixture. Next, the water phase components were heated and dissolved to prepare a water phase part, which was added to the aforementioned mixture, and the mixture was emulsified in a stirring process. As a result thereof, a sunscreen cream (Formulation Example 1), a sunscreen lotion (Formulation Example 2), a makeup base (Formulation Example 3), a BB cream (Formulation Example 4), a foundation (Formulation Example 5) and a hairspray base solution (Formulation Example 6) were each obtained. Regarding Formulation Example 6, a sunscreen hairspray was produced by mixing the hairspray base solution with LP gas at a 1:1 ratio, and forming an aerosol.

Formulation Example 1. Sunscreen Cream

TABLE 3

| | Blended amount |
|---|---|
| Hydrophobically treated talc | 5 |
| Polymethyl silsesquioxane | 2 |
| (Vinyl dimethicone/methicone silsesquioxane) cross-polymer | 5 |
| Hydrophobically treated zinc oxide (particle size 25 nm) | 10 |
| Hydrophobically treated titanium oxide (particle size 15 × 50 nm) | 5 |
| Octocrylene | 3 |
| Ethylhexyl methoxycinnamate | 5 |
| bis-Ethylhexyloxyphenol methoxyphenyl triazine | 1 |
| Diethylaminohydroxybenzoyl hexyl benzoate | 1 |
| Distearyl dimonium chloride | 0.5 |
| PEG-9 polydimethylsiloxyethyl dimethicone | 2 |
| PEG-10 dimethicone | 1 |
| Polyglyceryl-2 diisostearate | 0.2 |
| Distearyl dimonium hectorite | 2.2 |
| Dextrin palmitate | 1 |
| PPG-17 | 1 |
| Trimethylsiloxysilicic acid | 1 |
| Isododecane | 3 |
| Dimethicone | 10 |
| Isostearic acid | 1 |
| Alkyl ($C_{12-15}$) benzoate | 3 |
| Isopropyl myristate | 2 |
| Glycerin | 1 |
| Dipropylene glycol | 3 |
| Ethanol | 6 |
| EDTA-3Na | s.a. |
| Sodium chloride | s.a. |
| Water | bal |

Formulation Example 2. Sunscreen Lotion

TABLE 4

| | Blended amount |
|---|---|
| Hydrophobically treated talc | 7 |
| Methyl methacrylate cross-polymer | 5 |
| (Vinyl dimethicone/methicone silsesquioxane) cross-polymer | 3 |
| Hydrophobically treated zinc oxide (particle size 25 nm) | 10 |
| Hydrophobically treated titanium oxide (particle size 15 × 50 nm) | 5 |
| Dimethylsilylated silica | 0.5 |
| Octocrylene | 3 |
| Ethylhexyl methoxycinnamate | 5 |
| bis-Ethylhexyloxyphenol methoxyphenyl triazine | 1 |
| Diethylaminohydroxybenzoyl hexyl benzoate | 1 |
| Distearyl dimonium chloride | 0.2 |
| PEG-9 polydimethylsiloxyethyl dimethicone | 1.5 |
| Distearyl dimonium hectorite | 0.4 |
| Dextrin palmitate | 1 |
| PPG-17 | 1 |
| Trimethylsiloxysilicic acid | 1 |
| Isododecane | 3 |
| Dimethicone | 20 |
| Isostearic acid | 1 |
| Alkyl ($C_{12-15}$) benzoate | 3 |
| Isopropyl myristate | 5 |
| Glycerin | 1 |
| Ethanol | 10 |
| EDTA-3Na | s.a. |
| Sodium chloride | s.a. |
| Dipotassium glycyrrhizinate | 0.01 |
| Water | bal |

Formulation Example 3. Makeup Base

TABLE 5

| | Blended amount |
|---|---|
| Hydrophobically treated talc | 7 |
| Methyl methacrylate cross-polymer | 5 |
| Hydrophobically treated zinc oxide (particle size 25 nm) | 5 |
| Hydrophobically treated pigment-grade titanium oxide | 2 |
| Hydrophobically treated red iron oxide | s.a. |
| Hydrophobically treated yellow iron oxide | s.a. |
| Hydrophobically treated black iron oxide | s.a. |
| Octocrylene | 1 |
| Ethylhexyl methoxycinnamate | 5 |
| bis-Ethylhexyloxyphenol methoxyphenyl triazine | 1 |
| Diethylaminohydroxybenzoyl hexyl benzoate | 1 |
| Distearyl diinonium chloride | 0.5 |
| PEG-9 polydimethylsiloxyethyl dimethicone | 1.5 |
| Distearyl dimonium hectorite | 2 |
| Dextrin palmitate | 1 |
| PPG-17 | 1 |
| Diisopropyl sebacate | 3 |
| Trimethylsiloxysilicic acid | 1 |
| Isododecane | 7 |
| Dimethicone | 16 |
| Diphenylsiloxyphenyl trimethicone | 3 |
| Isostearic acid | 1 |
| Isopropyl myristate | 5 |
| Glycerin | 1 |
| Ethanol | 10 |
| EDTA-3Na | s.a. |
| Sodium chloride | s.a. |
| Water | bal |

Formulation Example 4. BB Cream

TABLE 6

| | Blended amount |
|---|---|
| Hydrophobically treated talc | 5 |
| Methyl methacrylate cross-polymer | 3 |
| (Vinyl dimethicone/methicone silsesquioxane) cross-polymer | 3 |
| Hydrophobically treated zinc oxide (particle size 25 nm) | 5 |
| Hydrophobically treated titanium oxide (particle size 15 × 50 nm) | 2 |
| Hydrophobically treated pigment-grade titanium oxide | 4 |
| Hydrophobically treated red iron oxide | s.a. |
| Hydrophobically treated yellow iron oxide | s.a. |
| Hydrophobically treated black iron oxide | s.a. |
| Octocrylene | 1 |
| Ethylhexyl methoxycinnamate | 7 |
| bis-Ethylhexyloxyphenol methoxyphenyl triazine | 1 |
| Diethylaminohydroxybenzoyl hexyl benzoate | 1 |
| Distearyl dimonium chloride | 0.5 |
| PEG-9 polydimethylsiloxyethyl dimethicone | 1.5 |
| Sorbitan sesquiisostearate | 1 |
| Distearyl dimonium hectorite | 2 |
| Dextrin palmitate | 1 |
| PPG-17 | 1 |
| Tri(trimethylsiloxy)silylpropyl carbamic acid pullulan | 0.3 |
| Trimethylsiloxysilicic acid | 1 |
| Dimethicone cross-polymer | 1 |
| (Dimethicone/phenylvinyl dimethicone) cross-polymer | 1 |
| Isododecane | 3 |
| Dimethicone | 12 |
| Isostearic acid | 0.55 |
| Isopropyl myristate | 5 |
| Glycerin | 1 |
| 1,3-Butylene glycol | 2 |
| Dipropylene glycol | 2 |
| Ethanol | 10 |
| EDTA-3Na | s.a. |
| Sodium chloride | s.a. |
| Water | bal |

Formulation Example 5. Foundation

TABLE 7

| | Blended amount |
|---|---|
| Hydrophobically treated talc | 5 |
| Methyl methacrylate cross-polymer | 2 |
| Hydrophobically treated zinc oxide (particle size 25 nm) | 5 |
| Hydrophobically treated titanium oxide (particle size 15 × 50 nm) | 2 |
| Hydrophobically treated pigment-grade titanium oxide | 5 |
| Hydrophobically treated red iron oxide | s.a. |
| Hydrophobically treated yellow iron oxide | s.a. |
| Hydrophobically treated black iron oxide | s.a. |

TABLE 7-continued

|  | Blended amount |
|---|---|
| (Dimethicone/vinyl dimethicone) cross-polymer | 0.2 |
| Octocrylene | 3 |
| Ethylhexyl methoxycinnamate | 5 |
| bis-Ethylhexyloxyphenol methoxyphenyl triazine | 0.3 |
| Diethylaminohydroxybenzoyl hexyl benzoate | 0.5 |
| Distearyl dimonium chloride | 0.3 |
| PEG-9 polydimethylsiloxyethyl dimethicone | 1.5 |
| Sorbitan sesquiisostearate | 1 |
| Distearyl dimonium hectorite | 0.5 |
| Dextrin palmitate | 1 |
| PPG-17 | 1 |
| Trifluoroalkyl dimethyl trimethylsiloxysilicic acid | 1 |
| Trimethylsiloxysilicic acid | 1 |
| Diphenylsiloxyphenyl trimethicone | 1 |
| Isododecane | 3 |
| Dimethicone | 10 |
| Cyclopentasiloxane | 10 |
| Isostearic acid | 1 |
| Isopropyl myristate | 5 |
| Glycerin | 1 |
| Xylitol | 0.2 |
| Ethanol | 10 |
| EDTA-3Na | s.a. |
| Sodium chloride | s.a. |
| Water | bal |

Formulation Example 6. Hairspray

TABLE 8

|  | Blended amount |
|---|---|
| Hydrophobically treated talc | 7 |
| Methyl methacrylate cross-polymer | 5 |
| Polysilicone-15 | 5 |
| Octocrylene | 5 |
| Ethylhexyl methoxycinnamate | 5 |
| bis-Ethylhexyloxyphenol methoxyphenyl triazine | 1 |
| Diethylaminohydroxybenzoyl hexyl benzoate | 2 |
| Distearyl dimonium chloride | 0.3 |
| PEG-9 polydimethylsiloxyethyl dimethicone | 1.5 |
| Distearyl dimonium hectorite | 0.3 |
| Dextrin palmitate | 2 |
| PPG-17 | 1 |
| Trimethylsiloxysilicic acid | 2 |
| Isododecane | 5 |
| Dimethicone | 10 |
| PBG/PPG-9/1 copolymer | 1 |
| Alkyl ($C_{12-15}$) benzoate | 3 |
| Diisopropyl sebacate | 5 |
| Isopropyl myristate | 5 |
| Sucrose tetrastearate triacetate | 1 |
| Glyceryl tri-2-ethylhexanoate | 5 |
| Isostearic acid | 0.5 |
| Glycerin | 1 |
| Xylitol | 1 |
| Ethanol | 10 |
| EDTA-3Na | s.a. |
| Sodium chloride | s.a. |
| Water | bal |

The invention claimed is:

1. A water-in-oil emulsion cosmetic, comprising:
    (A) 4% to 10% by mass of hydrophobically treated talc that is in flaky form;
    (B) 8% to 30% by mass of one or more ultraviolet absorbing agents selected from the group consisting of octocrylene, ethylhexyl methoxycinnamate, bis-ethylhexyloxyphenol methoxyphenyl triazine and diethylaminohydroxybenzoyl hexyl benzoate;
    (C) 0.1% to 1% by mass of distearyl dimonium chloride as a cationic surfactant;
    (E) 0.1% to 3% by mass of distearyl dimonium hectorite;
    (F) 0.6% to 3% by mass of PEG-9 polydimethylsiloxyethyl dimethicone;
    (G) 0.5% to 4% by mass of dextrin fatty acid ester;
    oils; and
    water.
2. The cosmetic, according to claim 1, further comprising:
    (D) 5% to 15% by mass of an ultraviolet scattering agent.

* * * * *